United States Patent
Taylor et al.

(10) Patent No.: US 8,075,530 B2
(45) Date of Patent: Dec. 13, 2011

(54) INSTRUMENT SEAL WITH INVERTING SHROUD

(75) Inventors: Scott V. Taylor, Mission Viejo, CA (US); Kimball B. McGinley, Laguna Niguel, CA (US); Henry Kahle, Trabuco Canyon, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 0 days.

(21) Appl. No.: 12/408,571

(22) Filed: Mar. 20, 2009

(65) Prior Publication Data

US 2009/0240204 A1 Sep. 24, 2009

Related U.S. Application Data

(60) Provisional application No. 61/038,379, filed on Mar. 20, 2008.

(51) Int. Cl.
*A61M 5/178* (2006.01)
(52) U.S. Cl. .............. 604/167.06; 604/167.01
(58) Field of Classification Search .......... 606/108, 606/185; 604/158, 162, 164.01, 164.1, 167.01, 604/167.02, 167.03, 167.04, 167.06, 192
See application file for complete search history.

(56) References Cited

U.S. PATENT DOCUMENTS

| | | | | |
|---|---|---|---|---|
| 5,895,377 A | * | 4/1999 | Smith et al. | 604/256 |
| 7,470,255 B2 | * | 12/2008 | Stearns et al. | 604/167.06 |
| 2005/0273133 A1 | | 12/2005 | Shluzas et al. | |
| 2006/0264991 A1 | * | 11/2006 | Johnson et al. | 606/167 |
| 2007/0027453 A1 | | 2/2007 | Hart et al. | |
| 2007/0088277 A1 | | 4/2007 | McGinley et al. | |
| 2008/0065021 A1 | * | 3/2008 | Jenkins et al. | 604/167.02 |

OTHER PUBLICATIONS

International Searching Authority/US, International Search Report and The Written Opinion of the International Searching Authority dated May 27, 2009, for International Application No. PCT/US2009/037863, filed Mar. 20, 2009, titled "Instrument Seal with Inverting Shroud".

* cited by examiner

*Primary Examiner* — Christopher D Koharski
(74) *Attorney, Agent, or Firm* — Rimas T. Lukas; Patrick Y. Ikehara; Pui Tong Ho

(57) ABSTRACT

A surgical access device comprising an instrument access channel extending through an instrument seal and a shroud comprising an inverting region disposed distally of the instrument seal exhibits improved tear-resistance of the instrument seal from instrument manipulation, for example, instrument withdrawals. Some embodiments of the inverting region invert through the instrument seal on instrument withdrawal. Some embodiments of the inverting region induce at least a portion of the instrument seal itself to invert on instrument withdrawal.

17 Claims, 8 Drawing Sheets

INSTRUMENT SEAL WITH INVERTING SHROUD

CROSS-REFERENCE TO RELATED APPLICATION

This application claims the benefit of U.S. Application No. 61/038,379, filed Mar. 20, 2008, the disclosure of which is incorporated by reference.

BACKGROUND

1. Technical Field

This application generally relates to medical devices, and more particularly, to an access device useful in laparoscopic surgery.

2. Description of the Related Art

Laparoscopic surgery is a type of reduced or minimally invasive surgery in which instruments access the interior of a patient's body through one or more access devices, for example, trocars. Trocars typically include a septum seal, which provides a fluid-tight seal with an instrument inserted therethrough, thereby preventing fluid leakage into or out of the patient's body. In laparoscopic procedures of the abdomen, the abdomen is typically inflated or insufflated with an insufflation gas, for example, carbon dioxide, a condition that is known as pneumoperitoneum. The insufflation gas lifts the abdominal wall away from the organ bed, thereby providing a surgeon with an improved surgical field. Manipulating an instrument, in particular, withdrawing an instrument can tear the septum seal. Tearing the septum seal can result in high leakage rates of the insufflation gas, e.g., carbon dioxide, and potentially, a complete loss of pneumoperitoneum. A seal withstands multiple laparoscopic instrument exchanges without tearing would better maintain pneumoperitoneum.

SUMMARY OF THE INVENTION

A surgical access device comprising an instrument access channel extending through an instrument seal and a shroud comprising an inverting region disposed distally of the instrument seal exhibits improved tear-resistance of the instrument seal from instrument manipulation, for example, instrument withdrawals. Some embodiments of the inverting region invert through the instrument seal on instrument withdrawal. Some embodiments of the inverting region induce at least a portion of the instrument seal itself to invert on instrument withdrawal.

Accordingly, some embodiments provide a surgical access device comprising a proximal end; a distal end; an instrument access channel extending through the access device from the proximal end to the distal end; an instrument seal comprising an opening substantially aligned with the instrument access channel; and a shroud substantially aligned with the instrument access channel, an inverting portion thereof disposed distally of the opening in the instrument seal, the shroud comprising an aperture through the inverting portion. The access device is convertible between a first state and a second state; in the first state, the inverting portion of the shroud is not inverted; in the second state, the inverting portion of the shroud is inverted, thereby protecting the instrument seal from damage by an instrument; and moving an instrument proximally in the access channel converts the access device from the first state to the second state.

In some embodiments, the surgical access device is a trocar comprising a seal assembly and a cannula, and the instrument seal and the inverting shroud are disposed in the seal assembly.

In some embodiments, the instrument seal comprises a gel seal. In some embodiments, the instrument seal comprises a septum seal. Some embodiments further comprise a seal shield proximal of the septum seal. In some embodiments, the shroud is disposed on and moves with the septum seal. In some embodiments, the shroud floats relative to the instrument seal.

Some embodiments further comprise a zero seal substantially aligned with the instrument channel. In some embodiments, the zero seal comprises at least one of a duckbill valve and a double-duckbill valve.

In some embodiments, the shroud comprises at least one of a polyolefin, polyethylene, polypropylene, polyvinyl chloride (PVC), polyvinylidene chloride, polytetrafluoroethylene (PTFE), polyester, polyamide, aramid (Kevlar®), polyimide, polyether block amide, fluorinated polymers, polyurethane, polyether, rubber, synthetic rubber, silicone, ethylene propylene diene monomer (EPDM), ethylene-propylene copolymer (EP rubber), polyisoprene, polybutadiene, polyurethane, styrene-butadiene, ethylene vinyl acetate (EVA), polychloroprene, perfluoroelastomer, and thermoplastic elastomer.

In some embodiments, the shroud comprises at least one of a slit, a slot, a hole, and a vent. In some embodiments, the inverting portion of the shroud converges frustoconically to the aperture. In some embodiments, the inverting portion of the shroud is substantially cylindrical. In some embodiments, the aperture of the shroud seals against the instrument extending therethrough.

In some embodiments, in the second state, at least a portion of the inverting element of the shroud extends through the instrument seal. In some embodiments, in the second state, the inverting element of the shroud inverts at least a portion of the instrument seal.

Some embodiments provide method for protecting an instrument seal from damage from withdrawal of an instrument therefrom, the method comprising: disposing an inverting shroud comprising an inverting portion distal of an opening in an instrument seal, wherein the inverting shroud comprises an aperture through the inverting region, the aperture substantially aligned with an instrument access channel extending through the opening in instrument seal, and withdrawing an instrument inverts the inverting region, thereby protecting the instrument seal from damage therefrom.

In some embodiments, protecting the instrument seal from damage comprises encasing the instrument access channel through the instrument seal with the inverting region. In some embodiments, protecting the instrument seal from damage comprises inducing a portion of the instrument seal around the instrument access channel to invert.

Some embodiments provide a surgical access device comprising a proximal end; a distal end; an instrument access channel extending through the access device from the proximal end to the distal end; an instrument seal substantially aligned with the instrument access channel; and a means for protecting the instrument seal from damage on withdrawing an instrument from the instrument access channel.

DETAILED DESCRIPTION OF CERTAIN EMBODIMENTS

The detailed description describes embodiments in which an inverting shroud is used in a trocar-type access device. Those skilled in the art will understand that in other embodiments, the inverting shroud is used in another type of surgical access device or system, for example, in a hand port, a single-port access system, and/or a limited port access system.

Figure 1A:
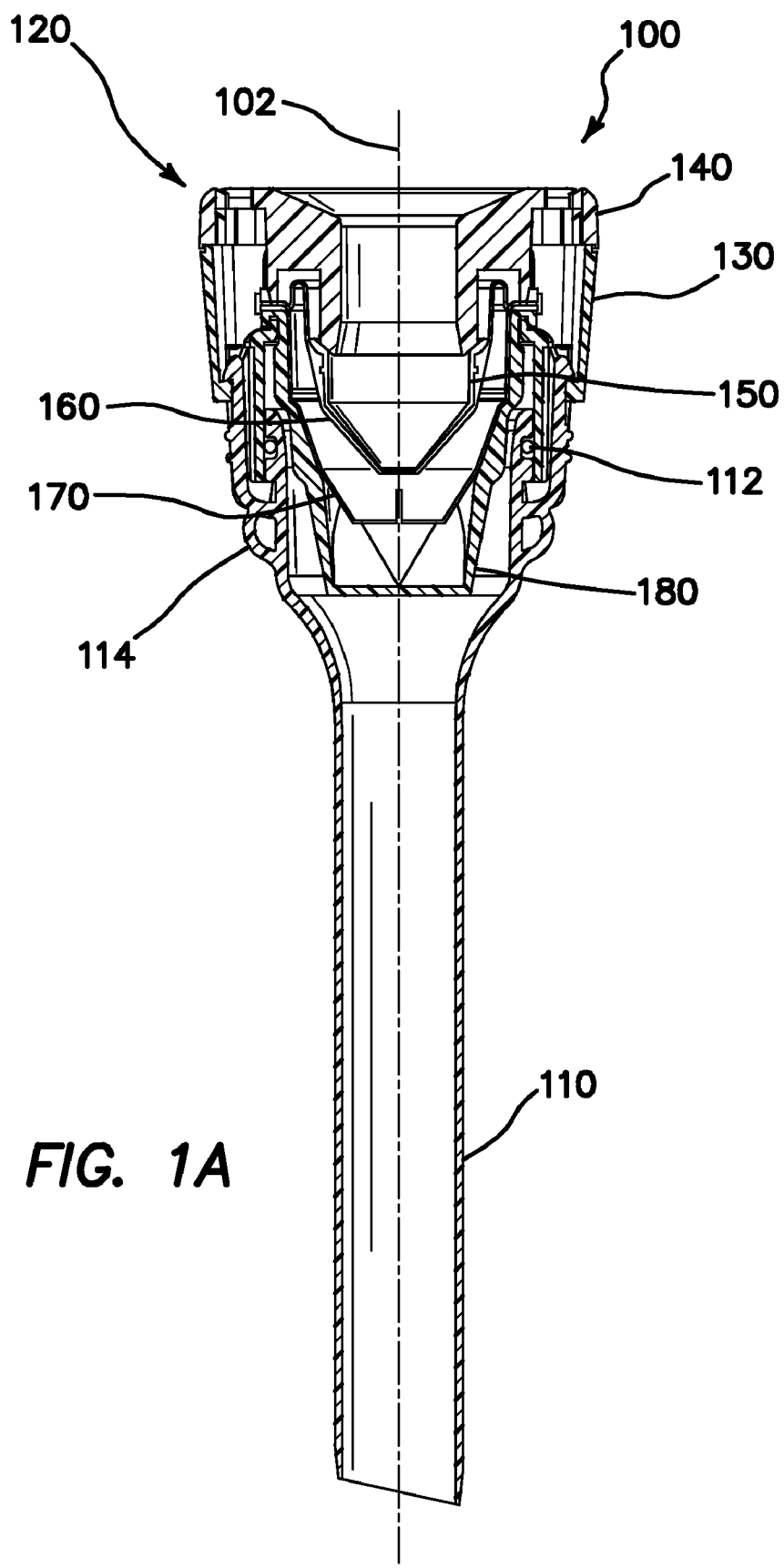
FIG. 1A is a side cross section of an embodiment of a surgical access device comprising an embodiment of an inverting shroud.

FIG. 1A is a longitudinal cross section of an embodiment of a surgical access device 100 in the form of a trocar comprising a proximal end, a distal end, and a longitudinal axis extending from the proximal end to the distal end. An instrument access channel 102 coincides with the longitudinal axis in the illustrated embodiment. The surgical access device comprises a tubular cannula 110 comprising a lumen aligned with the access channel 102, and a seal assembly 120 disposed at a proximal end of the cannula 110. In the illustrated embodiment, the cannula 110 and seal assembly 120 are releasably coupled. In other embodiments, the cannula 110 and seal assembly 120 are integrated. An O-ring 112 captured at the proximal end of the cannula 110 provides a fluid seal between the cannula 110 and the seal assembly 120 in the illustrated embodiment. In the illustrated embodiment, the proximal end of the cannula 110 further comprises a plurality of suture ties 114. Embodiments of the cannula 110 are rigid or flexible.

Figure 1B:
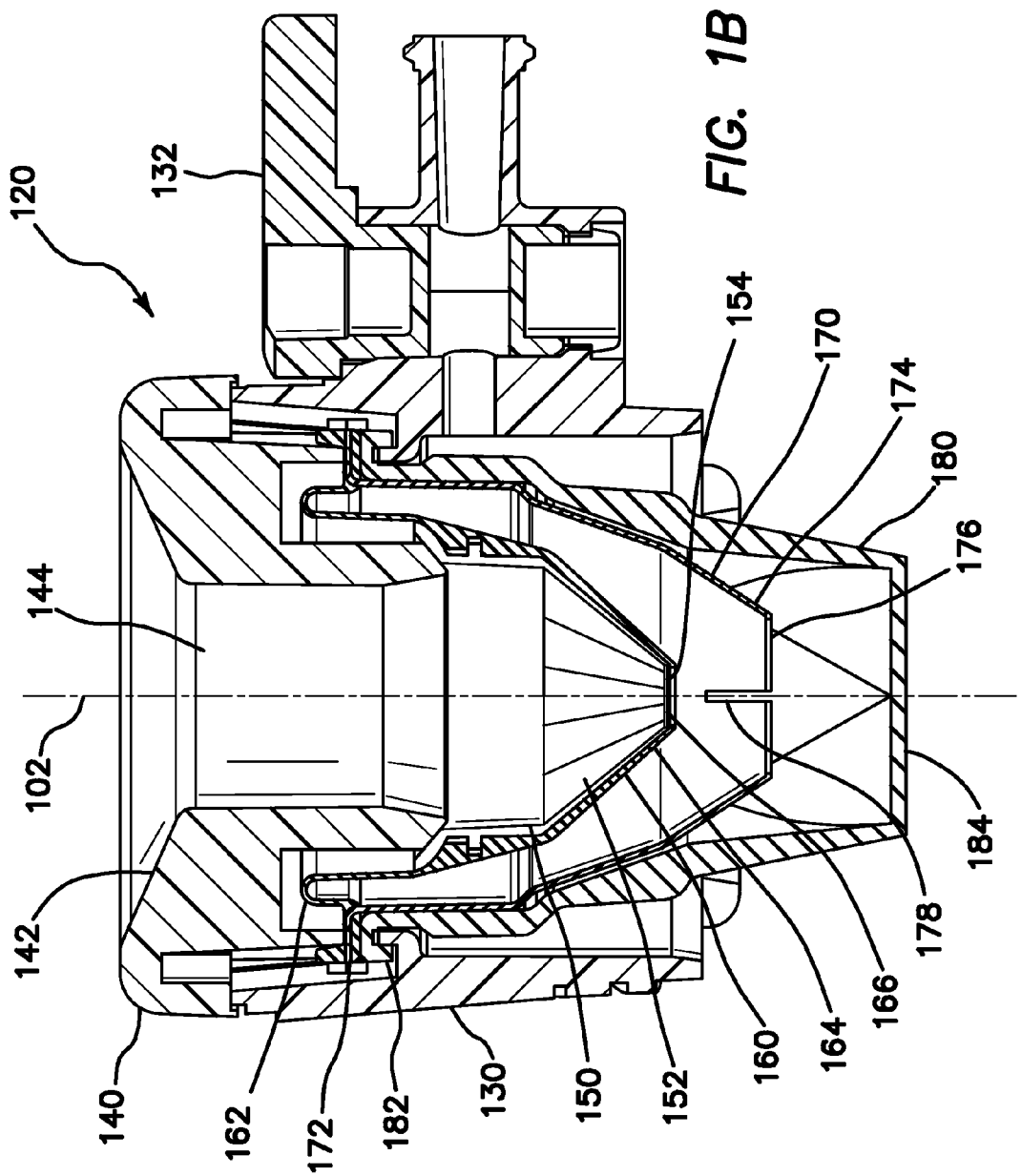
FIG. 1B is a cross section of a sealing assembly of the access device illustrated in FIG. 1A.

FIG. 1B is a longitudinal cross section of the seal assembly 120 taken through axis B-B in FIG. 1A. The seal assembly 120 comprises a seal housing 130 on which is disposed a fluid connector 132. In the illustrated embodiment, the fluid connector 132 comprises a Luer fitting and a stopcock. A cap or cover 140 closes a proximal end of the seal housing 132, securing within the housing 130, a seal shield 150, an instrument seal 160, an inverting shroud 170, and a zero seal 180. In the illustrated embodiment, the longitudinal axis and access channel 102 extend through the seal housing 130 the cap 140, the seal shield 150, the instrument seal 160, the inverting shroud 170, and the duckbill valve 180.

In the illustrated embodiment, the cap 140 comprises a funneled entry 142 disposed at a proximal end thereof, and an alignment channel 144 distal of the funneled entry 142. The funneled entry 142 guides instruments into the access channel 102, while the alignment channel 144 generally aligns an inserted instrument longitudinally with the access channel 102. Aligning the instrument with the access channel reduces instrument contact with off-axis portions of the device 100 or components thereof, thereby reducing damage thereto. The cap 140 is secured to the proximal end of the housing 130 using any suitable method, for example, mechanically (e.g., screw threads, clips, bayonet mounts, screws, latches, ratchets, pins, lock rings), adhesively (e.g., glue, epoxy, urethane, cyanoacrylate, pressure sensitive adhesive, polyvinyl alcohol adhesive, butadiene-styrene adhesive), welding (e.g., thermal, solvent, electron beam, laser, ultrasonic), magnetically, and the like. In some embodiments, the cap 140 is secured to the housing 130 by a combination of methods.

The cannula 110, housing 130, and cap 140 independently comprise suitable biologically compatible materials or combinations thereof, for example, metal, stainless steel, aluminum, nickel-titanium alloy, polymer resin, polycarbonate, polyester, polyamide (NYLON®, DELRIN®), aramid (KEVLAR®), polyimide, polyether block amide (PEBAX®), polyolefin, polyethylene (SPECTRA®), polypropylene, fluorinated polymers, epoxy, polystyrene, rubber, synthetic rubber, silicone, ethylene propylene diene monomer (EPDM), ethylene-propylene copolymer (EP rubber), polyisoprene, polybutadiene, polyurethane, styrene-butadiene, ethylene vinyl acetate (EVA), polychloroprene (NEOPRENE®), perfluoroelastomer (KALREZ®), polyvinyl chloride, polyvinylidene chloride, polycarbonate, polyvinyl chloride (PVC), polysulfone, polyetheretherketone (PEEK), polyepoxide, polyacrylate, polyether, acrylonitrile-butadiene-styrene (ABS), thermoplastic elastomer (HYTREL®, PELLETHANE®, KRATON®, C-FLEX®), glass, ceramic, carbon fiber, and the like. Some embodiments of suitable materials comprise copolymers, mixtures, blends, and/or alloys. Some embodiments of suitable materials comprise a composite, for example, a fiber reinforced polymer. Those skilled in the art will understand that different portions of a component comprise different materials in some embodiments.

The illustrated embodiment comprises an optional seal shield 150, which reduces damage to the instrument seal 160, for example from contact with a tip of an instrument inserted off-axis into the access channel 102. The illustrated embodiment of the seal shield 150 comprises a distal guide portion 152 that converges in a distal opening 152 aligned with the access channel 102. In the illustrated embodiment, the guide portion 152 is generally frustoconical, defining a funnel entry that guides the tips of instruments to the opening 154 during insertion. Some embodiments of the seal shield 150 comprise features that improve the guiding function, for example, longitudinal ribs or pleats disposed on the guide portion 152. The illustrated seal shield 150 is secured to the septum shield 160. Accordingly, the opening 154 in the seal shield 150 maintains alignment with an instrument opening 166 in the instrument shield 160 because the seal shield 150 moves in concert therewith. Embodiments of the seal shield comprise at least one of metal, stainless steel, polymer resin, polyolefin, polyethylene, polypropylene, polyvinyl chloride (PVC), polytetrafluoroethylene (PTFE, TEFLON®), polyamide (NYLON®, DELRIN®), copolymers, blends, mixtures, and the like. Some embodiments of the seal shield 150 are not elastomeric.

The instrument seal 160 provides an instrument seal with instruments over a range of diameters. In the illustrated embodiment, the instrument seal 160 comprises a septum seal. The instrument seal 160 comprises a radial flange 162 at a proximal end. The flange 160 extends inwardly from at or near an inner wall of the housing 130, towards the longitudinal axis. In the illustrated embodiment, the flange 162 comprises a convolution or bellows, which permits the instrument seal 160 to "float" or accommodate radial movement of an instrument extending therethrough. The convolution in the illustrated embodiment also provides the instrument seal 160 with a degree of longitudinal movement in response to longitudinal instrument motion. A sealing portion 164 of the instrument seal converges to an opening 166 aligned with the instrument channel 102. In the illustrated embodiment, the sealing portion 164 is generally frustoconical, defining a funnel entry for instruments inserted therethrough. The sealing portion 164 seals against an instrument extending through the opening 166. Accordingly, at least the sealing portion 164 of the instrument seal comprises an elastomeric material.

Those skilled in the art will understand that in other embodiments, the septum seal 160 has a different configuration, for example, a disk shape rather than a cone shape. Other embodiments use another type of instrument seal, for example, a gel seal.

The inverting shroud 170 in the illustrated embodiment comprises a radial flange 172 at a proximal end thereof, and an inverting region 174 that converges to a distal aperture or opening 176 aligned with the access channel 102. The flange 172 of the shroud extends inwardly from at or near the inner wall of the housing 130, towards the longitudinal axis. Some embodiments of the flange 172 comprise a convolution or bellows that allows the shroud 170 to float or move axially and/or laterally in response to instrument movements and/or movement of the septum seal 160 therein. The shroud 170 then extends longitudinally to the inverting region 174, which in the illustrated embodiment, is generally frustoconical, thereby defining a funnel entry for instruments. In other embodiments, the inverting region 174 has another shape, for example, cylindrical. The shroud 170 is longer than the septum seal 160. Accordingly, no part of the septum seal 160 extends through the aperture 176 of the shroud.

In some embodiments, the shroud 170 is suspended, for example, on elastomeric bands and/or springs, which permit lateral and/or axial movement of the shroud 170 within the seal assembly 120.

Embodiments of the access device 100 accommodate a wide range of instrument sizes, for example, with diameters of about 1 mm-16 mm or about 1 mm-25 mm. Other embodiments of the access device 100 accommodate a narrower range of instrument sizes, for example, with diameters of about 1 mm-5 mm, about 10 mm-12 mm, or about 10 mm-16 mm.

A diameter of the aperture 176 of the shroud is at least as large as a diameter of the opening 166 of the septum seal. Accordingly, the shroud 170 does not contact instruments at a smaller end of the designed size range of the access device 100 that are aligned with the longitudinal axis. For example, for a trocar with an instrument range of 5 mm to 15 mm, the aperture 176 of the inverting shroud does not contact a 5 mm instrument aligned with the longitudinal axis.

The illustrated embodiment of the inverting region 174 further comprises one or more slits or slots 178 extending from the aperture 176 proximally into the inverting region 174. The slits reduce a drag force between the inverting shroud and large-diameter cylindrical instruments such as laparoscopes, thereby preventing the inverting region 174 of the shroud inverting when used with these types of instruments. A small-diameter aperture 176 facilitates inversion of the shroud 170 by irregular features on an instrument; however, the small-diameter aperture 176 also increases drag on instruments. Embodiments of the slits 178 reduce drag forces in embodiments comprising a small-diameter aperture 176, thereby retaining the ease of inversion. Embodiments of the slits 178 facilitate deflection of the inverting region 174 in response to contact with laparoscopic instruments, thereby reducing the likelihood of puncturing and/or tearing thereof, particularly by the tip of an instrument during the insertion thereof. Embodiments of the slits or slots 178 also relieve pressure from insufflation gas, which would otherwise compress the shroud 170 against an instrument, thereby increasing drag thereon. Some embodiments of the shroud 170 comprise one or more holes or vents as pressure reliefs.

Embodiments of the inverting shroud 170 have a wall thickness that allows pendulous movement of the septum seal 160 therein, for example, during off-axis manipulation of laparoscopic instruments.

Embodiments of the inverting region 174 of the shroud comprise a material with a lower coefficient of friction than the sealing portion 164 of the septum seal. Some embodiments of the inverting region 174 comprise a film. Some embodiments comprise a woven or non-woven fabric. Some embodiments comprise a composite, for example, a fabric embedded in a resin and/or a fiber reinforced polymer film. Embodiments of the inverting region 174 comprise an elastomeric material. Other embodiments of the inverting region 174 do not comprise an elastomeric material. Suitable materials for the inverting region 174 include one or more polymer resins, for example, polyolefin, polyethylene, polypropylene, polyvinyl chloride (PVC), polyvinylidene chloride, polytetrafluoroethylene (PTFE, TEFLON®), polyester, polyamide (NYLON®, DELRIN®), aramid (Kevlar®), polyimide, polyether block amide (PEBAX®), fluorinated polymers, polyurethane, polyether, rubber, synthetic rubber, silicone, ethylene propylene diene monomer (EPDM), ethylene-propylene copolymer (EP rubber), polyisoprene, polybutadiene, polyurethane, styrene-butadiene, ethylene vinyl acetate (EVA), polychloroprene (NEOPRENE®), perfluoroelastomer (KALREZ®), thermoplastic elastomer (HYTREL®), PELLETHANE®, KPATONT, C-FLEX®), copolymers, blends, mixtures, composites, and the like.

In some embodiments, the inverting shroud 170 comprises a single material. In other embodiments, different sub-components of the inverting shroud, for example, the flange 172 and the inverting region 174, comprise different materials. Embodiments of the inverting shroud 170 are manufactured by any suitable method, for example, transfer molding for polyisoprene or injection molding for silicone.

Some embodiments of the inverting shroud 170 further comprise a friction-reducing surface treatment and/or coating at least on portions that contact instruments. Examples of suitable surface treatments and/or coatings include at least one of a hydrophilic polymer, silicone oil emulsion, silicone oil, silicone grease, polytetrafluoroethylene (PTFE, TEFLON®), cyanoacrylate, mineral oil, glycerin, polyxylylene xylylene (PARYLENE®), plasma surface treatment, and chlorination treatment. Some embodiments of the inverting shroud 170 comprise a textured surface that reduces friction, for example, dots, bumps, ridges, stripes, and the like. Embodiments of the texture have a pattern or are random.

The zero seal 180 comprises a proximal flange 182 that extends inwardly from at or near the inner wall of the housing 130 towards the longitudinal axis and a duckbill valve or double duckbill valve 184 at a distal end thereof. The duckbill valve 184 is aligned with the access channel 102. The duckbill valve 184 seals in the absence of an instrument extending therethrough, thereby preventing gas flow through the access channel 102 in the absence of an instrument and loss of pneumoperitoneum. Some embodiments of the access device 180 do not comprise a zero seal, while in other embodiments, the instrument seal 160 is also a zero seal.

As illustrated in FIG. 1B, the flange 162 of the instrument seal, the flange 172 of the shroud, and the flange 182 of the zero seal are sandwiched between the cap 140 and the housing 130, thereby securing the instrument seal 160, the shroud 170, and the zero seal 180. In some embodiments, the flanges 162, 172, 182 seal against each other, the cap 140 and the housing 130, thereby preventing or reducing gas leaks therethrough.

Each of the instrument seal 160, the shroud 170, and the zero seal 180 extends distally from their respective flanges 162, 172, and 182, and are nested, with the distal ends spaced to permit the unencumbered operation of each component. The seal shield 150 is nested in the instrument seal 160 in the illustrated embodiment. A diameter of each of the seal shield 150, the instrument seal 160, and the shroud 170 converge or taper from the proximal end to the distal end thereof with an opening or aperture aligned with the access channel 102 at the distal end thereof.

Figure 1C:
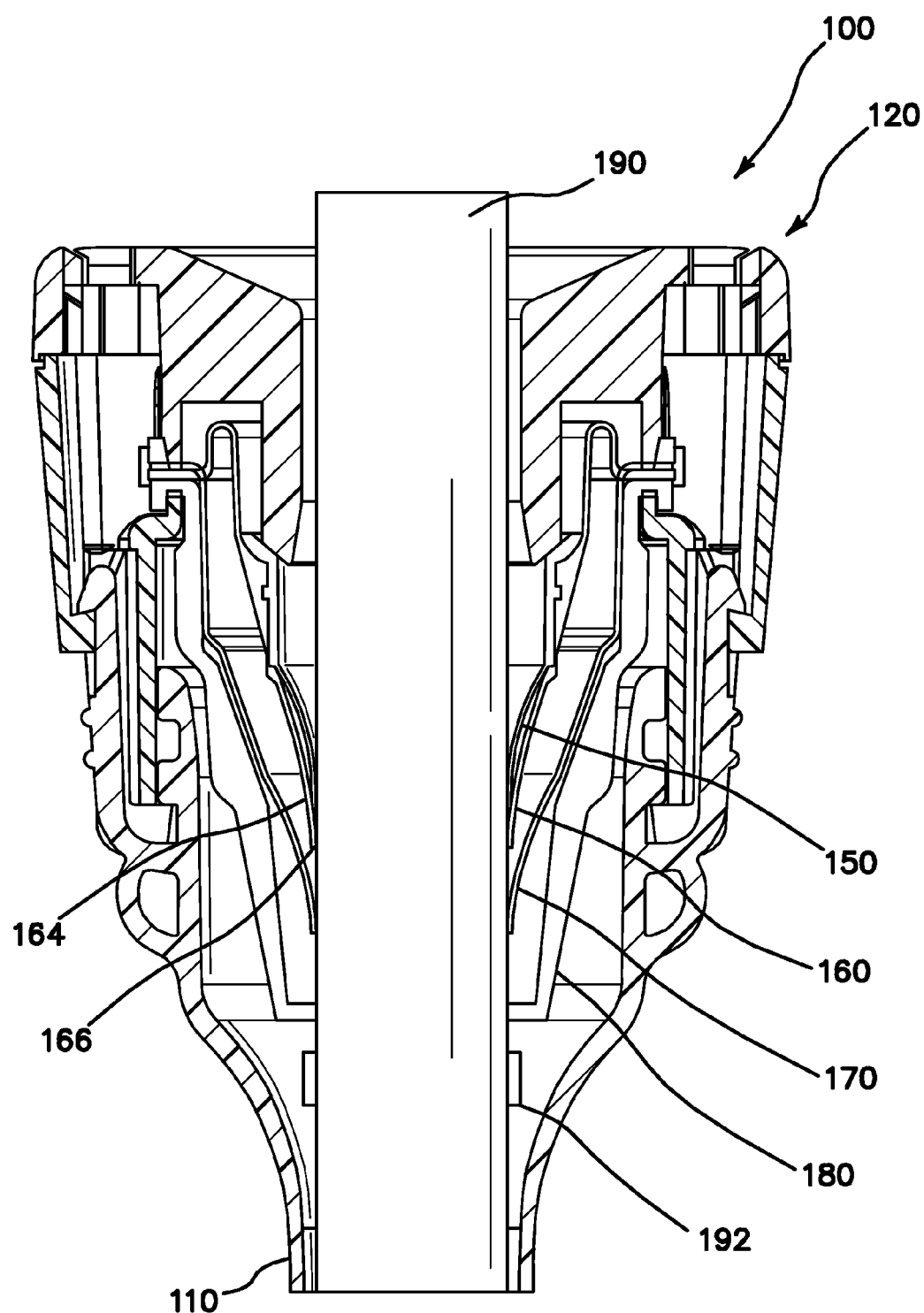
FIG. 1C is a detailed cross section of a proximal portion of the access device illustrated in FIG. 1A with an instrument inserted therein.

FIG. 1C is a view of the proximal end of the access device 100, taken along the same section as FIG. 1A, with an instrument 190 inserted in the access channel 102, and through the seal shield 150, the instrument seal 160, the shroud 170, and zero seal 180. The instrument 190 comprises a protrusion 192, which is advanced past the seal assembly 120 and into the cannula 110 in FIG. 1C. Because sealing portion 164 of the septum seal defines a funnel entry to the opening 166, the protrusion 192 advances through the opening 166 without snagging or hanging-up thereon. As illustrated, the sealing portion 164 of the septum seal elongates distally and radially, to conform to the shaft of the instrument 190, thereby forming a fluid-tight seal therewith. The inverting region 174 of the shroud also conforms to the shaft of the instrument 190 in the illustrated embodiment.

Figure 1D:
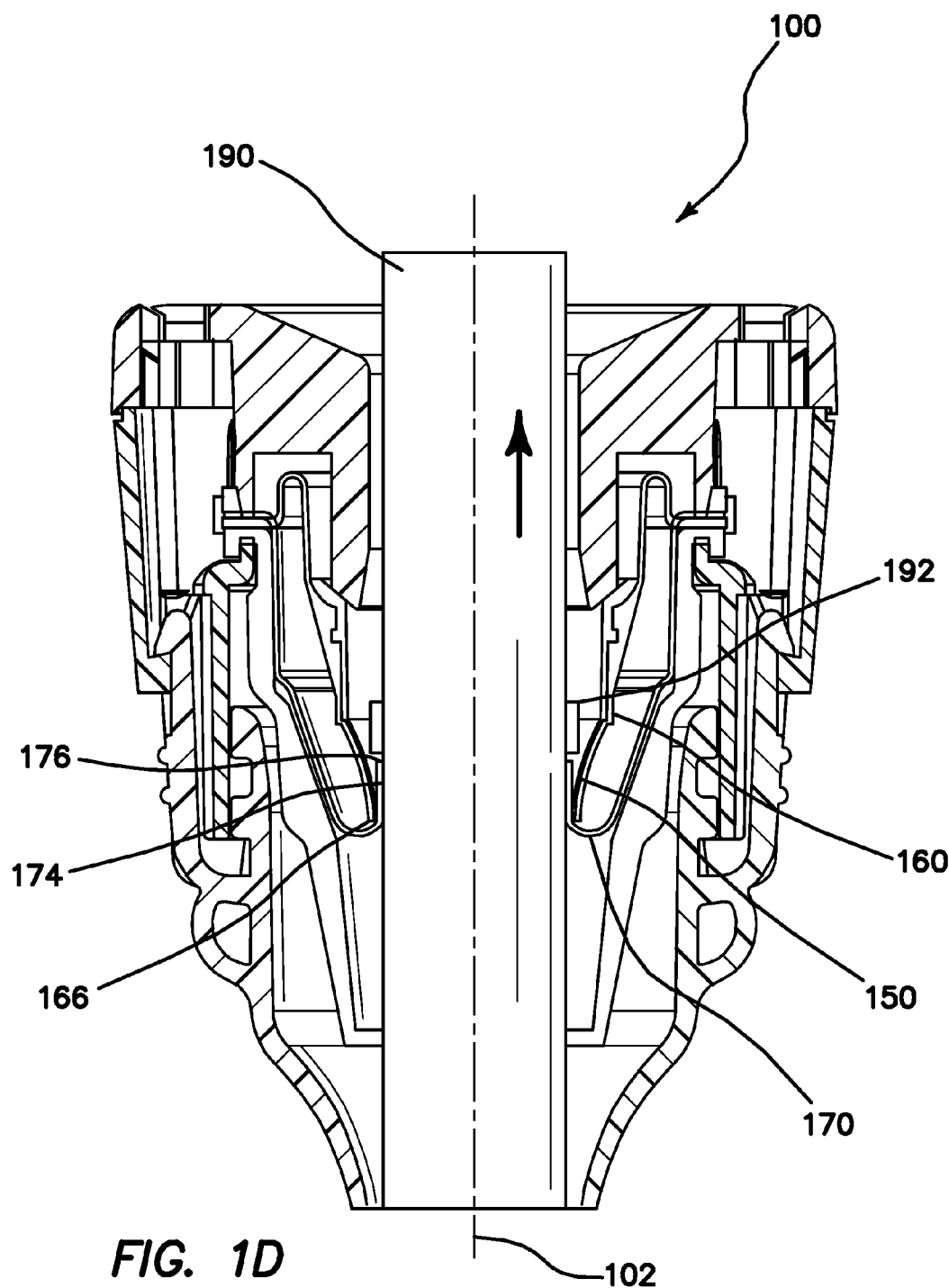
FIG. 1D is a cross section of an embodiment of the device illustrated in FIG. 1C with the instrument partially withdrawn.

As shown in FIG. 1D, which is the same view of the access device 100 as shown in FIG. 1C with the instrument 190 partially withdrawn therefrom, the inverting shroud 170 is arranged and configured to reduce or prevent tearing of an instrument seal such as the illustrated septum seal 150 during the withdrawal and/or manipulation of a laparoscopic instrument 190. In the illustrated view, on withdrawing the instrument protrusion 192 past the opening 166 of the septum seal, the protrusion 192 has snagged or captured the aperture 176 of the shroud, thereby inverting the inverting portion 174 thereof. On continued withdrawal of the instrument 190, the protrusion 192 draws the inverting portion 174 of the shroud through the opening 166 of the septum seal, thereby protecting or shielding the opening 166 of the septum shield from the protrusion 192 by lining or encasing the opening 166. Consequently, the inverting portion 174 reduces or prevents damage, such as tearing, to the opening 166 of the septum seal 160. In the illustrated embodiment, the inverting portion 174 of the shroud also extends through the opening 154 in the seal shield. Examples of instrument features that will induce the inverting region 174 of the shroud to invert include irregular tips such as L-hook monopolar electrodes and J-hook monopolar electrodes.

In the illustrated embodiment, an axial length of the inverting portion 174 of the shroud is sufficient to extend through the opening 166 of the septum seal in the inverted configuration. The inverting portion 174 of the shroud inverts during the withdrawal and/or manipulation of a laparoscopic instrument 190 with irregular features, which draw the inverting portion 174 through the opening 166 of the septum seal, effectively encasing the opening 166 of the septum seal therein in a protective funnel that guides the laparoscopic instrument 190 through the opening 166 of the septum seal. In the illustrated embodiment, the septum seal 160 and septum shield 150 do not invert. Only the inverting portion 174 of the shroud inverts in the illustrated embodiment. With the inverting portion 174 of the shroud drawn through the opening 166 of the septum seal, irregular features of a laparoscopic instrument will not catch and/or tear the opening 166 of the septum seal. After the laparoscopic instrument 190 is completely withdrawn from the seal assembly 120, the inverting portion 174 of the shroud reverts to the non-inverted configuration illustrated in FIG. 1B, driven by the resilient material thereof. Changing the direction of the instrument 190 in the access channel 102 will also revert the inverting portion 174 to the non-inverting configuration in some embodiments.

Figure 1E:
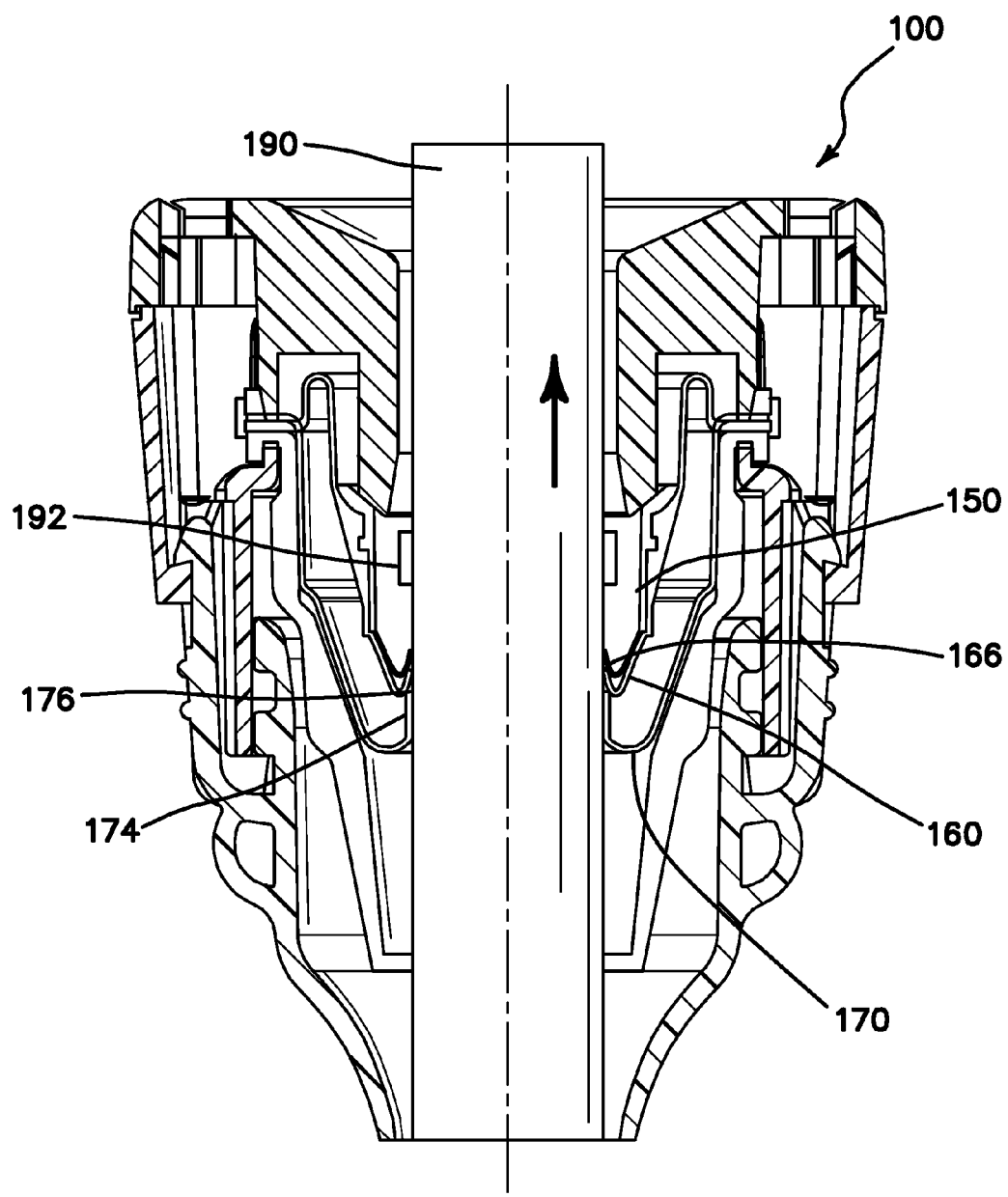
FIG. 1E is a cross section of another embodiment of the device illustrated in FIG. 1C with the instrument partially withdrawn.

FIG. 1E illustrates a cross section of another embodiment of an access device 100 in which the instrument 190 is partially withdrawn compared with the configuration illustrated in FIG. 1C. As in the embodiment illustrated in FIG. 1D, withdrawing an instrument 190 comprising an irregularity, in the illustrated embodiment, a protrusion 192, induces inversion of the inverting portion 174 of the shroud. The protrusion 174 catches the aperture 176 of the shroud, thereby inverting the inverting portion 174, which then contacts the opening 166 and/or surrounding sealing portion 164 of the septum seal, thereby urging the sealing portion 164 of the septum seal around the opening 166. In some embodiments, a portion of the seal shield 150 around the opening 154 also inverts. In the illustrated embodiment, the inverting portion 174 of the shroud does not extend through the opening 166 of the septum seal. In other embodiments, the inverting portion 174 of the shroud extends through opening 166 of the septum seal, thereby encasing and protecting the opening 166 of the septum seal, as discussed above. In the embodiment illustrated in FIG. 1E in which the inverting portion 174 of the shroud does not extend through the opening 166 of the septum seal, the inverted portion of the septum seal 160 itself funnels the laparoscopic instrument 190 through the septum seal opening 166 as it is withdrawn. The rolled over edge of the inverted portion of the septum seal 160 is less susceptible to catching and tearing compared with the edge of the opening 166 of a non-inverted septum seal 160. In embodiments in which the inverting portion 174 of the shroud extends through the opening 166 of the septum seal, the inverting portion 174 of the shroud encases the opening 166 of the septum seal, thereby defining a protective funnel that guides the laparoscopic instrument 190 through the opening 166 of the septum seal as the instrument 190 is withdrawn.

Some embodiments of the inverting portion 174 of the shroud comprises ribs or other reinforcing and/or stiffening members that collide with the portion of the septum seal 160 around the opening 166, thereby facilitating the inversion thereof.

In some embodiments, a uniformly-shaped laparoscopic instrument such as a laparoscope does not invert the inverting shroud 170. In embodiments in which the inverting shroud 170 urges the septum seal 160 and seal shield 150 to invert, withdrawing the uniformly-shaped instrument also does not invert these components. Drag force on the uniformly-shaped instrument is reduced during withdrawal thereof because the shroud 170, septum seal 160, and seal shield 150 remain in non-inverted configurations.

Embodiments of the inverting shroud 170 exhibit reduced the friction forces or drag forces associated with withdrawing a laparoscopic instrument. High drag forces produced experienced while withdrawing an instrument can result in inadvertent removal of the trocar cannula 110 and seal assembly 120 from the abdomen of the patient. As discussed above, when the inverting portion 174 of the shroud inverts and encases the opening 166 of the septum seal during instrument withdrawal, the septum seal 160 no longer directly contacts the instrument 190, which contacts only the inverting shroud 170. In embodiments in which the inverting shroud 170 has a lower coefficient of friction compared to the septum seal 160, the drag or frictional force on withdrawing the instrument is reduced. In some embodiments, the inverting portion 174 of the shroud in the inverted configuration seals a laparoscopic instrument 190, thereby effectively maintaining pneumoperitoneum as the instrument 190 is withdrawn.

FIGS. 2-5 are side cross sections of embodiments in which an inverting shroud is coupled, secured, or integrated with a septum seal.

Figure 2:
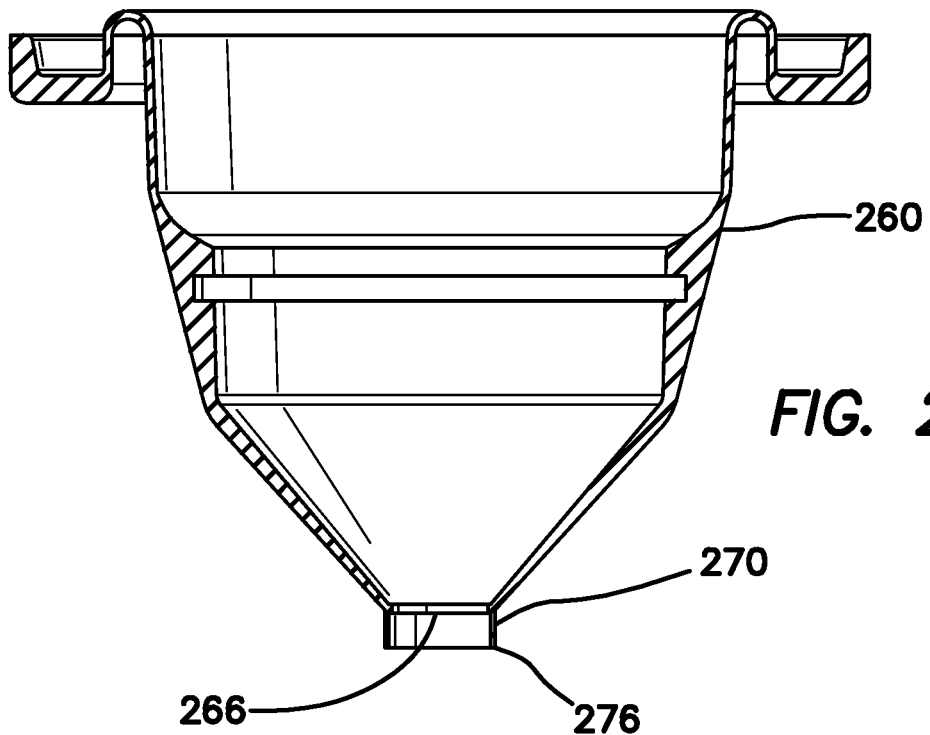
FIG. 2 is a cross section of an embodiment of a septum seal with an inverting shroud disposed thereon.

In the embodiment illustrated in FIG. 2, an inverting shroud 270 extends from a distal tip of a septum seal 260. In the illustrated embodiment, the inverting shroud 270 is disposed at the opening 266 of the septum seal. In some embodiments, the inverting shroud 270 is a separately manufactured component, which is then secured to the septum seal 260. In other embodiments, the inverting shroud 270 and septum seal 260 are integrated and manufactured as a single component, which reduces the number of steps and components in manufacturing the access device. In the illustrated embodiment, the inverting shroud 270 is dimensioned to enable the shroud 270 to invert and encase the opening 266 of the septum seal during instrument withdrawal, as discussed above.

In the illustrated embodiment, the shroud 270 is generally cylindrical. In other embodiments, the shroud 270 has another shape, for example, frustoconical. Also, as discussed above, some embodiments of the shroud 270 comprise one or more slits or slots. In some embodiments, the inverting shroud 270 is also a secondary seal for instruments with diameters larger than the diameter of the aperture 276 of the shroud, for example, greater than 10 mm for an access device designed to accommodate instruments with diameters of from about 5 mm to about 15 mm In the embodiment illustrated in FIG. 2, the shroud 270 moves in concert with the septum seal 260, thereby reducing the likelihood that the inverting shroud 270 will adversely interfere with the function and movement of the septum seal 260. Also, because the inverting shroud 270 moves in concert with the septum seal 260, the inverting shroud 270 does not contact instruments with diameters smaller than the aperture 276 of the inverting shroud when instruments pivot the septum seal 260 from the longitudinal axis of the access device.

Figure 3:
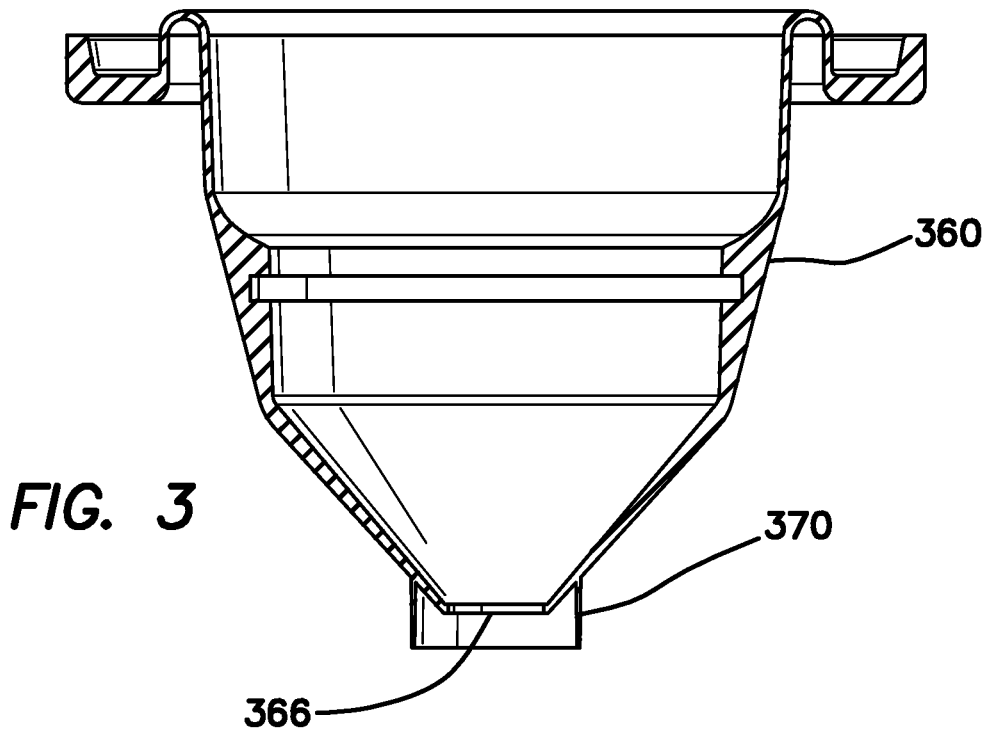
FIG. 3 is a cross section of an embodiment of a septum seal with an inverting shroud disposed thereon.

FIG. 3 illustrates another embodiment of a septum seal 360 on which an inverting shroud 370 is disposed. The embodiment illustrated in FIG. 3 is generally similar to the embodiment illustrated in FIG. 2, except that the inverting shroud 370 has a larger diameter, and consequently, is disposed farther from the opening 366. In the illustrated embodiment, inverting the shroud 370 encases the opening 366 of the septum seal. In some embodiments, inverting the shroud 370 also inverts the portion of the septum seal around the opening 366 within the perimeter of the shroud 270.

Figure 4:
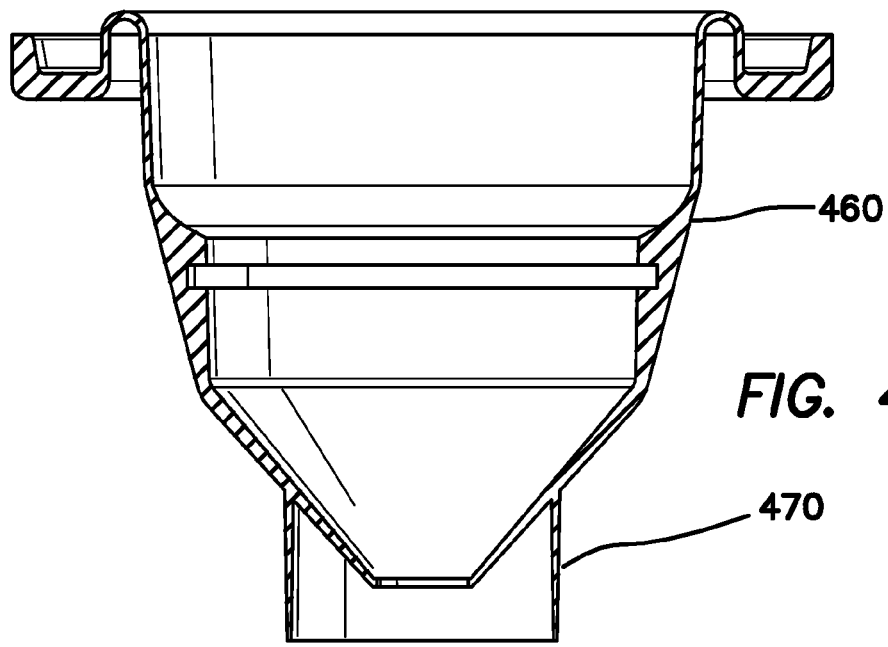
FIG. 4 is a cross section of an embodiment of a septum seal with an inverting shroud disposed thereon.

FIG. 4 illustrates another embodiment of a septum seal 460 on which an inverting shroud 470 is disposed. The embodiment illustrated in FIG. 4 is generally similar to the embodiments illustrated in FIGS. 2 and 3, except the inverting shroud 470 has an even larger diameter.

Figure 5:
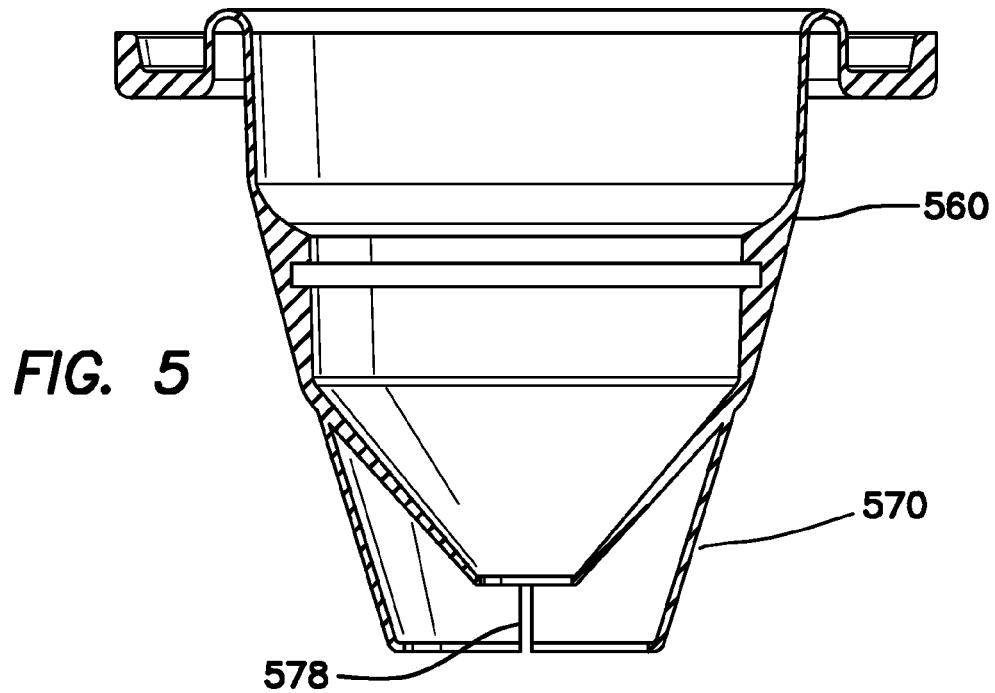
FIG. 5 is a cross section of an embodiment of a septum seal with an inverting shroud disposed thereon.

FIG. 5 illustrates another embodiment of a septum seal 560 on which an inverting shroud 570 is disposed. The embodiment illustrated in FIG. 5 is similar to the embodiments illustrated in FIGS. 2-4. In the illustrated embodiment, the shroud is generally frustoconical and comprises at least one slit 578. In some embodiments, the slits 578 define the shroud 570 as a plurality of strips or petals.

Figure 6:
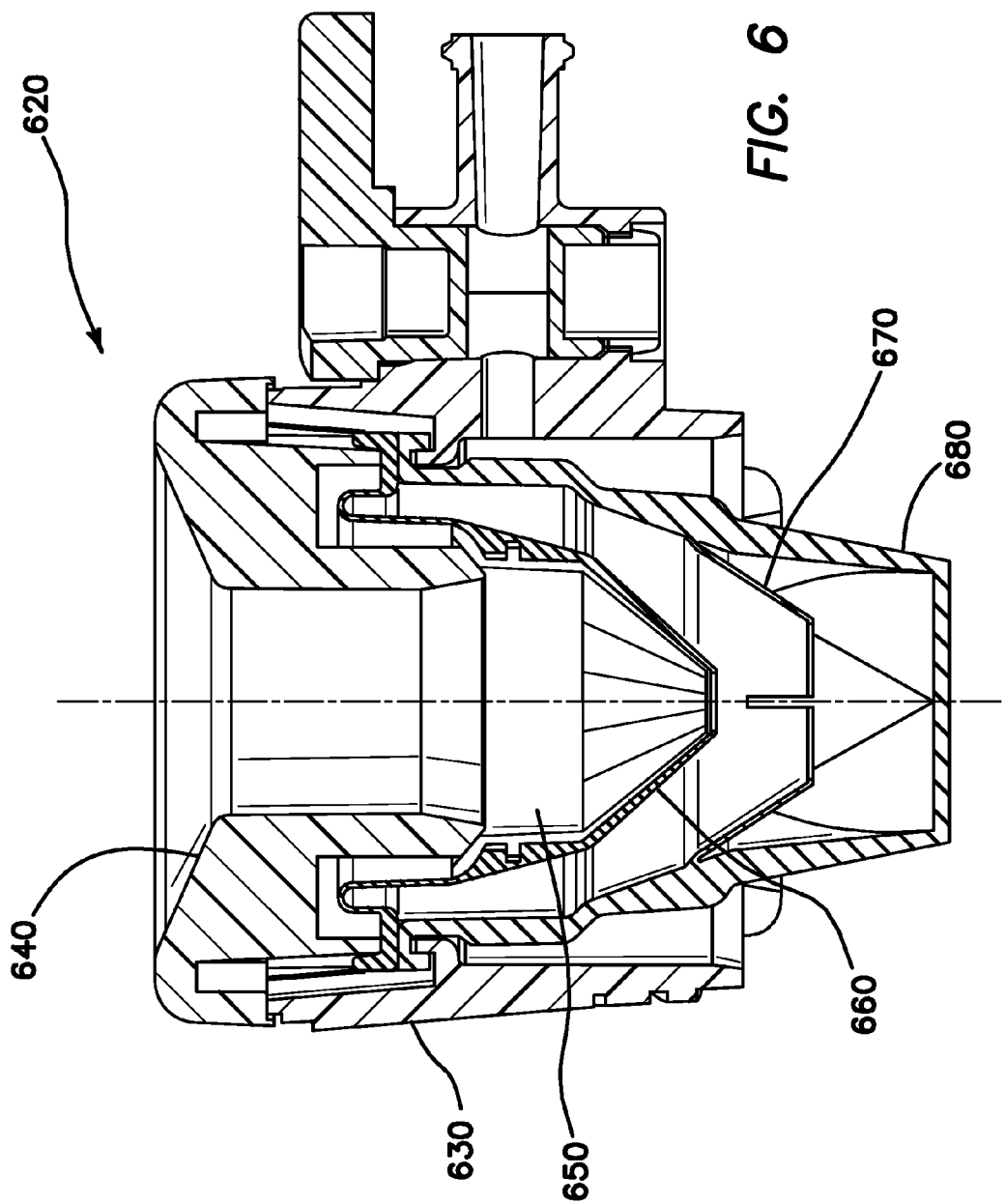
FIG. 6 is a cross section of an embodiment of a seal assembly comprising an embodiment of an inverting shroud disposed on a duckbill valve.

FIG. 6 illustrates an embodiment of a seal assembly 620 comprising a seal shield 650, a septum seal 660, an inverting shroud 670, and a duckbill valve 680 disposed in a seal housing 630 and secured therein by a cap 640. The seal assembly is similar to the embodiment illustrated in FIG. 1B, except that the inverting shroud 670 in the illustrated embodiment is disposed on the duckbill valve 680. In some embodiments, the inverting shroud 670 and duckbill valve 680 are manufactured separately, then assembled. In other embodiments, the inverting shroud 670 and the duckbill valve 680 are manufactured as a monolithic component.

While certain embodiments have been particularly shown and described with reference to exemplary embodiments thereof, it will be understood by those of ordinary skill in the art that various changes in form and details may be made therein without departing from the spirit and scope thereof as defined by the following claims.

What is claimed is:

1. A surgical access device comprising a proximal end; a distal end; an instrument access channel extending through the access device from the proximal end to the distal end; a seal housing having a cap providing entry to the access channel at the proximal end; an instrument seal comprising an opening substantially aligned with the instrument access channel and a sealing portion configured to seal against an instrument inserted into the opening; and a shroud substantially aligned with the instrument access channel, an inverting portion thereof disposed distally of the opening in the instrument seal, the shroud comprising an aperture through the inverting portion; the instrument seal being located between the seal housing cap and the shroud, wherein the access device is convertible between a first state and a second state;

in the first state, the inverting portion of the shroud is not inverted;

in the second state, the inverting portion of the shroud is inverted and contacts the instrument seal, thereby protecting the instrument seal from damage by an instrument; and moving an instrument proximally in the access channel converts the access device from the first state to the second state.

2. The surgical access device of claim 1, wherein the surgical access device is a trocar comprising a seal assembly and a cannula, and the instrument seal and the inverting shroud are disposed in the seal assembly.

3. The surgical access device of claim 1, wherein the instrument seal comprises a gel seal.

4. The surgical access device of claim 1, wherein the instrument seal comprises a septum seal.

5. The surgical access device of claim 4, further comprising a seal shield proximal of the septum seal.

6. The surgical access device of claim 4, wherein the shroud is disposed on and moves with the septum seal.

7. The surgical access device of claim 1, wherein the shroud floats relative to the instrument seal.

8. The surgical access device of claim 1, further comprising a zero seal substantially aligned with the instrument channel.

9. The surgical access device of claim 8, wherein the zero seal comprises at least one of a duckbill valve and a double-duckbill valve.

10. The surgical access device of claim 1, wherein the shroud comprises at least one of a polyolefin, polyethylene, polypropylene, polyvinyl chloride (PVC), polyvinylidene chloride, polytetrafluoroethylene (PTFE), polyester, polyamide, aramid (Kevlar®), polyimide, polyether block amide, fluorinated polymers, polyurethane, polyether, rubber, synthetic rubber, silicone, ethylene propylene diene monomer (EPDM), ethylene-propylene copolymer (EP rubber), polyisoprene, polybutadiene, polyurethane, styrene-butadiene, ethylene vinyl acetate (EVA), polychloroprene, perfluoroelastomer, and thermoplastic elastomer.

11. The surgical access device of claim 1, wherein the shroud comprises at least one of a slit, a slot, a hole, and a vent.

12. The surgical access device of claim 1, wherein the inverting portion of the shroud converges frustoconically to the aperture.

13. The surgical access device of claim 1, wherein the inverting portion of the shroud is substantially cylindrical.

14. The surgical access device of claim 1, wherein the aperture of the shroud seals against the instrument extending therethrough.

15. The surgical access device of claim 1, wherein in the second state, at least a portion of the inverting element of the shroud extends through the instrument seal.

16. The surgical access device of claim 1, wherein in the second state, the inverting element of the shroud inverts at least a portion of the instrument seal.

17. A surgical access device comprising a proximal end; a distal end; an instrument access channel extending through the access device from the proximal end to the distal end; a seal housing having a cap providing entry to the access channel at the proximal end; an instrument seal substantially aligned with the instrument access channel and having a sealing portion configured to seal against an instrument inserted into the opening; and a means for protecting the instrument seal from damage on withdrawing an instrument from the instrument access channel by contact with the instrument seal the instrument seal being located between the seal housing cap and said means for protecting the instrument seal.

* * * * *